US006639357B1

(12) United States Patent
Parthasarathy et al.

(10) Patent No.: US 6,639,357 B1
(45) Date of Patent: Oct. 28, 2003

(54) HIGH EFFICIENCY TRANSPARENT ORGANIC LIGHT EMITTING DEVICES

(75) Inventors: Gautam Parthasarathy, Princeton, NJ (US); Chihaya Adachi, East Windsor, NJ (US); Paul E. Burrows, Princeton Junction, NJ (US); Stephen R. Forrest, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/522,155

(22) Filed: Mar. 9, 2000

Related U.S. Application Data
(60) Provisional application No. 60/188,613, filed on Mar. 8, 2000, and provisional application No. 60/185,232, filed on Feb. 28, 2000.

(51) Int. Cl.$^7$ .............................. H01J 1/62; H05B 33/00
(52) U.S. Cl. .......................... 313/504; 313/506
(58) Field of Search ................................. 313/504, 503, 313/506; 428/690, 691

(56) References Cited

U.S. PATENT DOCUMENTS

| | | |
|---|---|---|
| 4,164,431 A | 8/1979 | Tang |
| 4,611,385 A | 9/1986 | Forrest et al. ................. 29/574 |
| 4,720,432 A | 1/1988 | Van Slyke et al. ........... 313/506 |
| 5,047,687 A | 9/1991 | VanSlyke |
| 5,059,862 A | 10/1991 | VanSlyke et al. |
| 5,315,129 A | 5/1994 | Forrest et al. ................. 257/21 |

(List continued on next page.)

FOREIGN PATENT DOCUMENTS

| | | | |
|---|---|---|---|
| EP | 1 076 368 | 2/2001 | ........... H01L/51/20 |
| JP | 10-050481 | * 2/1998 | ........... H05B/33/22 |
| WO | WO97/33296 | 9/1997 | ............. H01J/1/62 |

OTHER PUBLICATIONS

C.W. Tang, et al., "Organic Electroluminescent Diodes", 51 *Appl. Phys. Lett.*, 913 (1987). (Sep.).
S.R. Forrest, et al., "Organic Emitters Promise a New Generation of Displays", *Laser Focus World*, (Feb. 1995).
V. Bulovic, et al., "Transparent light–emitting devices" *Nature*, 380, p. 29 (1996). (Mar.).
Z. Shen, et al. "Three–Color, Tunable, Organic Light–Emitting Devices", *Science*, 276, pp. 2009–2011 (1997). (Jun.).
G. Parthasarathy, et al., "Metal–free cathode for organic semiconductor devices", *Appl. Phys. Lett.*, 72, pp. 2138–2140 (1998). (Apr.).
J. Kido, et al., "Bright organic electroluminescent devices having a metal–doped electron–injecting layer", *Applied Physics Letters*, v. 73, n.20, pp. 2866–2868 (1998). (Nov.).

(List continued on next page.)

Primary Examiner—Ashok Patel
Assistant Examiner—Karabi Guharay
(74) Attorney, Agent, or Firm—Kenyon & Kenyon

(57) ABSTRACT

A highly transparent non-metallic cathode is disclosed that comprises a metal-doped organic electron injection layer that is in direct contact with a transparent non-metallic electron injecting cathode layer, such as indium tin oxide (ITO), wherein the metal-doped organic electron injection layer also functions as an exciton blocking or hole blocking layer. The metal-doped organic electron injection layer is created by diffusing an ultra-thin layer of about 5–10 Å of a highly electropositive metal such as Li throughout the layer. A representative embodiment of the highly transparent non-metallic cathode comprises a layer of ITO, a layer of 2,9-dimethyl-4,7-diphenyl-1,10-phenanthroline (BCP), which acts as an electron injection, exciton blocking, and hole blocking layer, and an ultra-thin layer of lithium, which degenerately dopes the layer of BCP, improving the electron injecting properties of the BCP layer. This cathode is demonstrated for use in an OLED having a transparency of about 90% or higher combined with a device external quantum efficiency of about 1% or higher.

15 Claims, 8 Drawing Sheets

U.S. PATENT DOCUMENTS

| | | | |
|---|---|---|---|
| 5,399,936 A | 3/1995 | Namiki et al. | 313/504 |
| 5,554,220 A | 9/1996 | Forrest et al. | 117/88 |
| 5,677,572 A | 10/1997 | Hung et al. | |
| 5,703,436 A | 12/1997 | Forrest et al. | 313/506 |
| 5,707,745 A | 1/1998 | Forrest et al. | 428/432 |
| 5,714,838 A | 2/1998 | Haight et al. | 428/457 |
| 5,721,160 A | 2/1998 | Forrest et al. | 438/28 |
| 5,739,635 A | 4/1998 | Wakimoto | |
| 5,757,026 A | 5/1998 | Forrest et al. | 257/40 |
| 5,757,139 A | 5/1998 | Forrest et al. | 315/169.3 |
| 5,776,622 A | 7/1998 | Hung et al. | |
| 5,776,623 A | 7/1998 | Hung et al. | |
| 5,811,833 A | 9/1998 | Thompson | 257/40 |
| 5,834,893 A | 11/1998 | Bulovic et al. | 313/506 |
| 5,844,363 A | 12/1998 | Gu et al. | 313/506 |
| 5,861,219 A | 1/1999 | Thompson et al. | 428/690 |
| 5,874,803 A | 2/1999 | Garbuzov et al. | 313/506 |
| 5,917,280 A | 6/1999 | Burrows et al. | 313/506 |
| 5,922,396 A | 7/1999 | Thompson | 427/69 |
| 5,932,895 A | 8/1999 | Shen et al. | 257/40 |
| 5,937,272 A | 8/1999 | Tang | |
| 5,949,186 A | 9/1999 | Nagayama et al. | 313/504 |
| 5,953,587 A | 9/1999 | Forrest et al. | 438/99 |
| 5,981,306 A | 11/1999 | Burrows et al. | 438/22 |
| 5,986,268 A | 11/1999 | Forrest et al. | 250/372 |
| 5,986,401 A | 11/1999 | Thompson et al. | 313/504 |
| 5,998,803 A | 12/1999 | Forrest et al. | 257/40 |
| 6,005,252 A | 12/1999 | Forrest et al. | 250/458.1 |
| 6,010,796 A * | 1/2000 | Kijima | 313/504 |
| 6,013,384 A | 1/2000 | Kido et al. | |
| 6,013,538 A | 1/2000 | Burrows et al. | 438/22 |
| 6,013,982 A | 1/2000 | Thompson et al. | 313/506 |
| 6,064,151 A | 5/2000 | Choong et al. | 313/504 |
| 6,069,442 A | 5/2000 | Hung et al. | 313/504 |
| 6,137,223 A * | 10/2000 | Hung et al. | 313/506 |
| 6,140,763 A | 10/2000 | Hung et al. | |
| 6,172,459 B1 | 1/2001 | Hung et al. | |
| 6,278,236 B1 | 8/2001 | Madathil et al. | |

OTHER PUBLICATIONS

L.S. Hung, et al., "Interface engineering in preparation of organic surface–emitting diodes", *Applied Physics Letters*, v.74, n.21, pp. 3209–3211 (1999). (May).

N. Johansson, et al., "Electronic structure of tris (8–hydroxyquinoline) aluminum thin films in the pristine and reduced states", *J. Chem. Phys.*, 111, pp. 2157–2163 (1999). (Aug.).

G. Gu, et al., "Transparent stacked organic light emitting devices", *J. Appl. Phys.*, 86, pp. 4067–4075 (1999). (Oct.).

P. E. Burrows, et al., "Relationship between electroluminescence and current transport in organic heterojunction light–emitting devices", *J. Appl. Phys.*, 79, pp. 7991–8006 (1996). (May).

G. Parthasarathy, et al., "A full color transparent metal–free stacked organic light emitting device with simplified pixel biasing", *Adv. Mat.*, 11, pp. 907–910 (1999). (No month).

E.I. Haskal, et al., "Lithium–aluminum contacts for organic–light emitting devices", *Appl. Phys. Lett.*, 71, pp. 1151–1153 (Sep. 1, 1997).

Parthasarathy, et al., "A Highly Transparent Organic Light Emitting Device Employing a Metal–Free Cathode," Poster Session Abstract, Materials Research Fair, Princeton Materials Institute, Princeton University (Nov. 6, 1997).

Kido, et al., "Bright red light–emitting organic electroluminescent devices having a europium complex as an emitter," Appl. Phys. Lett., v.65 (1994) pp. 2124–2126. (Oct.).

Kido, et al., "White–light–emitting organic electroluminescent device using lanthanide complexes," Jpn. J. Appl. Phys., v.35 (1996) pp. L394–L396. (Mar.).

Kido, et al., "Multilayer white light–emitting organic electroluminescent device," Science, v.267 (1995) pp. 1332. (Mar.).

Kido, et al., "Electroluminescence in terbium complex," Chemistry Letters (1990) pp. 657–660. (No month).

Kido and K. Nagai, "Organic Electroluminescent Devices Using Lanthanide Complexes," Journal of Alloys and Compounds, vol. 192 (1993) pp. 30–33. (No month).

Hung, et al., "Enhanced electron injection in organic electroluminescence devices using an Al/LiF electrode," Appl. Phys. Lett. 70 (1997) pp. 152. (Jan.).

Forrest, et al., "Organic–on–inorganic semiconductor contact barrier diodes . . . ," J. Appl. Phys. 56 (1984) pp. 543. (Jul.).

Bulovic, et al., "Study of locilized and extended excitons in 3,4,9,10–perylenetetracarboxylic dianhydride (PTCDA) . . . ," Chem. Phys. 210 (1996) pp. 1–12. (No month).

Co–pending application Ser. No. 09/153,144, filed Sep. 14, 1998, entitled "Structure for High Efficiency Electroluminescent Device". (Now U.S. patent no. 6,097,147).

* cited by examiner

HIGH EFFICIENCY TRANSPARENT ORGANIC LIGHT EMITTING DEVICES

This application claims the benefit of Provisional application Ser. Nos. 60/185,232, filed Feb. 28, 2000, and 60/188,613, filed Mar. 8, 2000.

FIELD OF THE INVENTION

The present invention relates to highly efficient and highly transparent organic light emitting devices (OLEDs) using cathodes comprised of a transparent, non-metallic, electron injecting cathode layer, such as ITO, and a metal-doped organic electron injection layer that also functions as an exciton blocking layer and/or as a hole blocking layer.

BACKGROUND OF THE INVENTION

The field of optoelectronic devices includes those which convert electrical energy into optical energy and those which convert optical energy into electrical energy. Such devices include photodetectors, phototransistors, solar cells, light emitting devices and lasers. Such devices typically include a pair of electrodes, referred to as a anode and cathode and at least one charge-carrying layer sandwiched between the anode and cathode. Depending on the function of the optoelectronic device the charge-carrying layer or layers may be comprised of a material or materials that are electroluminescent in response to an applied voltage across the electrodes or the layer or layers may form a heterojunction capable of generating a photovoltaic effect when exposed to optical radiation.

In particular, organic light emitting devices (OLEDs) are usually comprised of several layers in which one of the layers is comprised of an organic material that can be made to electroluminesce in response to an applied voltage, C. W. Tang et al., *Appl. Phys. Lett.* 51, 913 (1987). Certain OLEDs have been shown to have sufficient brightness, range of color and operating lifetimes for use as a practical alternative to LCD-based full color flat-panel displays. S. R. Forest, P. E. Burrows and M. E. Thompson, *Laser Focus World*, February 1995. Some have sufficient transparency to be used in heads-up displays or in transparent windows and billboards. Significant commercial interest has been generated in a new type of display incorporating stacked organic light emitting devices that have the potential to provide high resolution, simple and inexpensive color displays and transparent color displays. V. Bulovic, G. Gu, P. E. Burrows, M. E. Thompson, and S. R. Forrest, *Nature*, 380, 29 (1996); U.S. Pat. No. 5,703,436, Forrest et al I. This transparent OLED (TOLED) had about 70% transparency when turned off, and it emitted light from both the top and bottom surfaces with a total device external quantum efficiency approaching 1% when the device was turned on. This TOLED used a transparent indium tin oxide (ITO) hole injecting layer as one electrode, the anode, and a Mg—Ag—ITO electron injecting layer as another electrode, the cathode. A transparency significantly greater than 70% would have been preferred, but the reflectance of the metal charge carrying layer prevented this.

A device was disclosed in which the ITO side of the Mg—Ag—ITO electrode was used as a hole injecting layer for a second, stacked TOLED. Additional layers could also be stacked, each layer being independently addressable and emitting a specified color. U.S. Pat. No. 5,707,745, Forest et al II, disclosed an integrated stacked, transparent OLED (SOLED) that allowed both intensity and color to be independently varied and controlled with an external power supply in a color tunable display device. Forrest et al II, thus, illustrates a principle for achieving integrated, full color pixels that provide high image resolution, which is made possible by the compact pixel size of a SOLED. Furthermore, fabrication costs are comparatively less than prior art methods, making displays made from SOLEDs commercially attractive.

Such devices whose structure is based upon the use of layers of organic optoelectronic materials generally rely on a common mechanism leading to optical emission. Typically, this mechanism is based upon the radiative recombination of injected electrons and holes. Specifically, OLEDs are comprised of at least two thin organic layers separating the anode and cathode of the device. The material of one of these layers is specifically chosen based on the material's ability to assist in injecting and transporting holes, a "hole transporting layer " (HTL), and the material of the other layer is specifically selected according to its ability to assist in injecting and transporting electrons, an "electron transporting layer " (ETL). In an optoelectronic device having at least one ETL and one HTL, the cathode is identified as the electrode on the ETL side of the device, and the anode is identified as the electrode on the HTL side of the device.

With such a construction, the device can be viewed as a diode with a forward bias when the potential applied to the anode is more positive than the potential applied to the cathode. Under these bias conditions, the anode injects holes (positively charged carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. A Frenkel exciton is formed when an electron and a hole localize on the same molecule. One may visualize this short-lived state as having an electron that can drop, "relax, " from fits conduction potential to a valence band, with relaxation occurring, under certain preferred conditions, by a photoemissive mechanism. Adopting this concept of the mechanism for operation of a typical thin-layer organic device, the electroluminscent flyer comprises a luminescence zone receiving mobile charge carriers (electrons and holes) from the electrodes (cathode and anode)

The materials that function as the electron transporting layer or as the hole transporting layer of the OLED are frequently the same materials that are incorporated into the OLED to produce the electroluminescent emission. If the HTL or ETL function as the emissive layer of such devices, then the OLED is referred to as having a single heterostructure. Alternatively, an OLED, having a separate layer of electroluminescent material included between the HTL and ETL, is referred to as having a double heterostructure. Thus, a heterostructure for producing electroluminescence may be fabricated as a single heterostructure or as a double heterostructure.

One of the shortcomings in these OLEDs has been the transparency of the cathode. A high quantum efficiency is achieved using a metal layer with a low work function, such as magnesium-silver (Mg—Ag), calcium, or a compound electrode such as LiF—Al or LiAl, but the metal layer must be made thin enough to achieve a satisfactory transparency, because metal layers are also highly reflective and absorptive in the visible region of the spectrum. For example, a conventional TOLED uses a 75–100 Å Mg—Ag layer capped with a thicker layer of transparent ITO deposited on it. Although a device with about 70% transmission may be obtained, there is still significant reflection from the compound cathode. In addition, in SOLEDs in which at least one of the color producing layers is contained between the metallic cathodes of adjacent color producing OLEDs, microcavity effects are present which can give rise to color tuning problems. Z. Shen, P. E. Burrows, V. Bulovic, S. R. Forrest, and M. E. Thompson, Science 276, 2009 (1997). Such microcavity effects may also lead to an undesired angular dependence of the emitted light. Furthermore, thin Mg—Ag layers are sensitive to atmospheric degradation; therefore, they require special designs and processing steps to be undertaken so as to preserve their effectiveness in functioning as the cathode of an OLED.

In OLEDs where a still higher level of transparency is desired, a compound cathode comprising a non-metallic cathode and an organic interface layer can be used. Parthasarathy, P. E. Burrows, V. Khalin. V. G. Kozlov, and S. R. Forrest, *Appl. Phys. Lett.* 72, 2138 (1998) ("Parthasarathy I"). Due to the absence of a metallic cathode layer, the representative $Alq_3$-based TOLEDs disclosed by Parthasarathy I emitted nearly identical light levels in the forward and back scattered directions. Optical transmission of at least about 85% was achieved using this non-metallic, compound cathode. However, the quantum efficiency of a device fabricated with such a cathode is typically reduced, in the range of about 0.1 to 0.3%, compared to OLEDS using the Mg—Ag—ITO cathode of Forrest et al I, wherein the device efficiency was about 1% but the transparency was only about 70% Therefore, the non-metallic cathode improves transparency but degrades device efficiency. A cathode that is both highly transparent and efficient would be preferred.

It is known that a metal doped organic layer can be used in an OLED as an electron injecting layer at the interface between a metal cathode and an emitter layer to increase quantum efficiency of the OLED. A lithium doped layer of tris-(8-hydroxyquinoline) aluminum ($Alq_3$) generates radical anions of $Alq_3$, serving as intrinsic electron carriers, which result in a low barrier height for electron injecting and high electron conductivity of the lithium doped $Alq_3$ layer. J. Kido and T. Matsumoto, *Applied Physics Letters*, v. 73, n.20, 2866 (1998). This improves quantum efficiency, but the device was not transparent.

A compound cathode comprising a layer of lithium-doped CuPc in contact with an emitter layer, such as α-napthylphenylbiphenyl (α-NPB), on one side and a layer of ITO, as a conductive layer, on the other side achieves an improved transparency and a slightly improved quantum efficiency, but lower efficiency than relatively non-transparent metal cathodes. L. S. Hung and C. W. Tang, *Applied Physics Letters*, v. 74, n.21, 3209 (1999).

It would be desirable if compound cathodes could be fabricated from materials that were as transparent as the compound cathodes using ITO and CuPc or lithium-doped CuPc, but with the quantum efficiency of a metal cathode. This would combine high efficiency and high transparency in a single compound cathode that could be used in highly efficient and highly transparent optoelectronic devices.

SUMMARY OF THE INVENTION

The present invention relates to highly efficient and highly transparent OLEDs employing highly transparent cathodes comprising a metal-doped organic electron injection layer that is in direct contact with a transparent, non-metallic, electron injecting cathode layer, wherein the metal-doped organic electron injection layer also functions as an exciton blocking layer and/or as a hole blocking layer.

In a specific aspect of the present invention, a layer of ITO is deposited on a lithium-doped organic electron injection layer.

More specifically, during fabrication of an OLED, an organic electron inspection layer may be doped with a metal either by depositing the organic electron injection, layer on an ultra-thin layer of lithium or by depositing the ultra-thin layer of lithium on the organic electron injection layer. Based on the thicknesses of the layers prepared in this manner, it is believed that the lithium diffuses entirely, from either direction, throughout the organic electron injection layer, thus forming a degenerately-doped organic electron injection layer. A layer of lithium could also be deposited on both sides of the organic electron injection layer, or the lithium could be co-deposited within the organic electron injection layer.

In a representative embodiment of the present invention, the organic electron injection layer comprises 2,9-dimethyl-4,7-diphenyl-1,10-phenanthroline (also called BCP or bathocuproine), which has the structural formula shown in FIG. 4.

One of the advantages of one present invention is that it provides a cathode that may be used in an OLED having a unique combination of high external quantum efficiency and high transparency over the entire visible spectrum.

Another advantage of the invention is that the highly efficient transparent cathode may be used to advantage in other types of optoelectronic devices.

DETAILED DESCRIPTION OF THE PREFERRED EMBODIMENTS OF THE INVENTION

Figure 1:
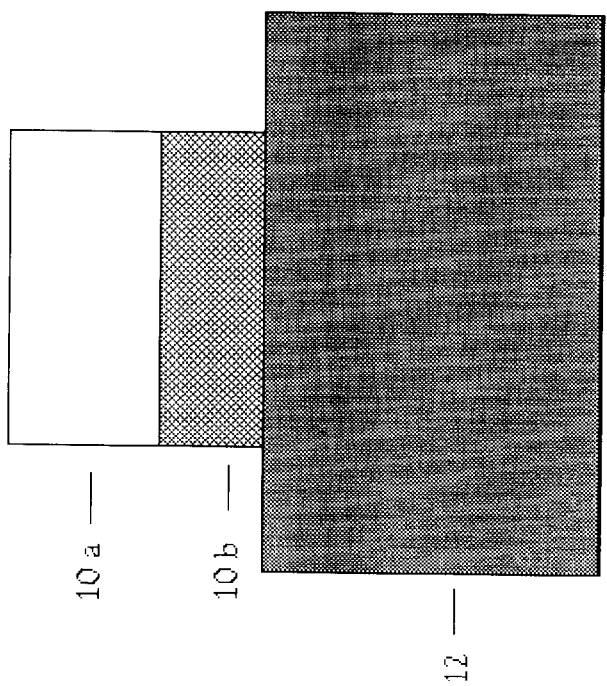
FIG. 1 shows an OLED, having a compound cathode with a transparent conduction layer 10*a*, an exciton blocking layer 10*b*, and the remainder of the OLED, 12, wherein the remainder comprises, for example, in sequence, an ETL, an optional separate emitting layer, an HTL, and an anode.
Figure 2:
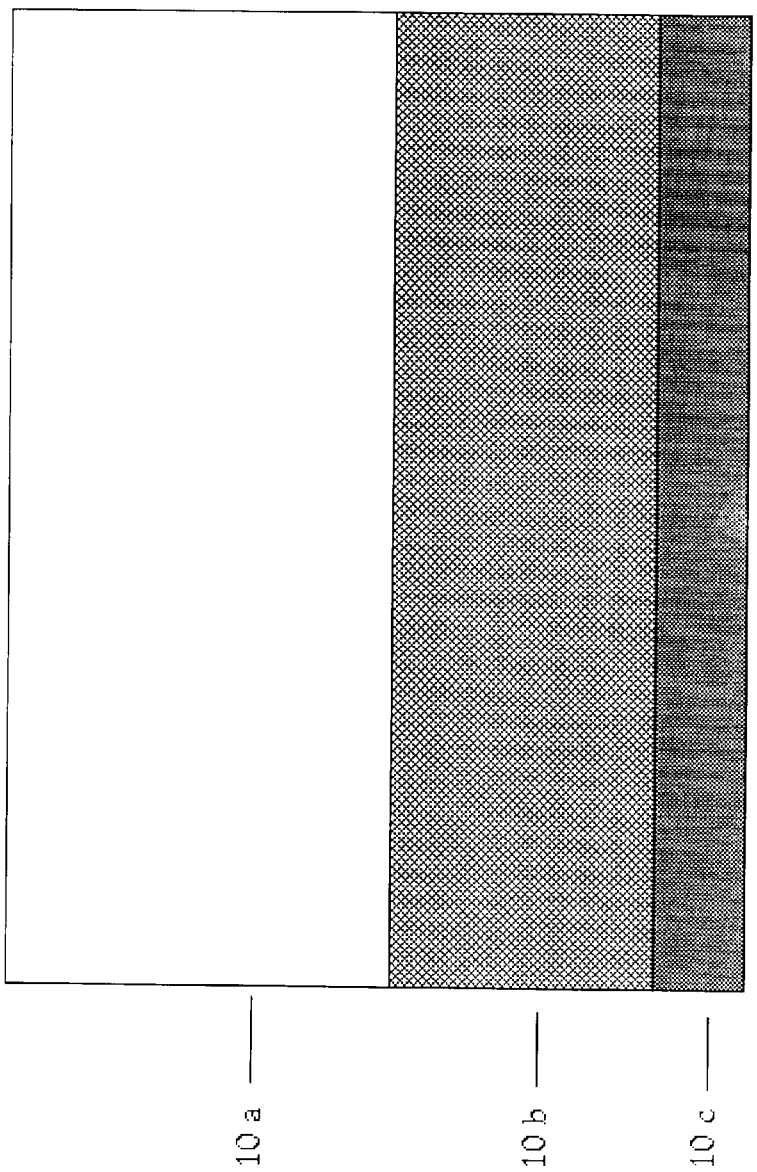
FIG. 2 shows a compound cathode comprising a transparent semiconducting layer, 10*a*, an exciton blocking layer, 10*b*, and a layer of metal for doping the exciton blocking layer, 10*c*.
Figure 3:
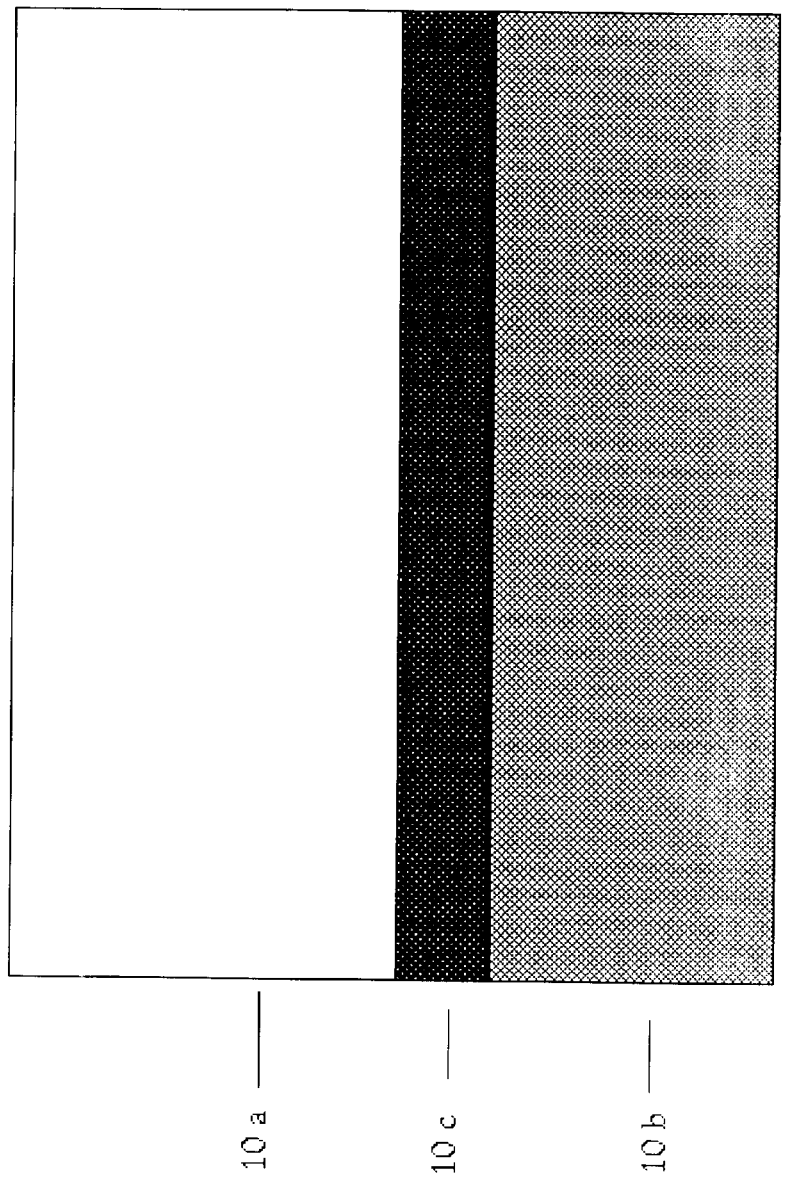
FIG. 3 shows a compound cathode comprising a transparent semiconducting layer, 10*a*, on a layer of metal, 10*c*, for doping an exciton blocking layer, 10*b*.
Figure 4:
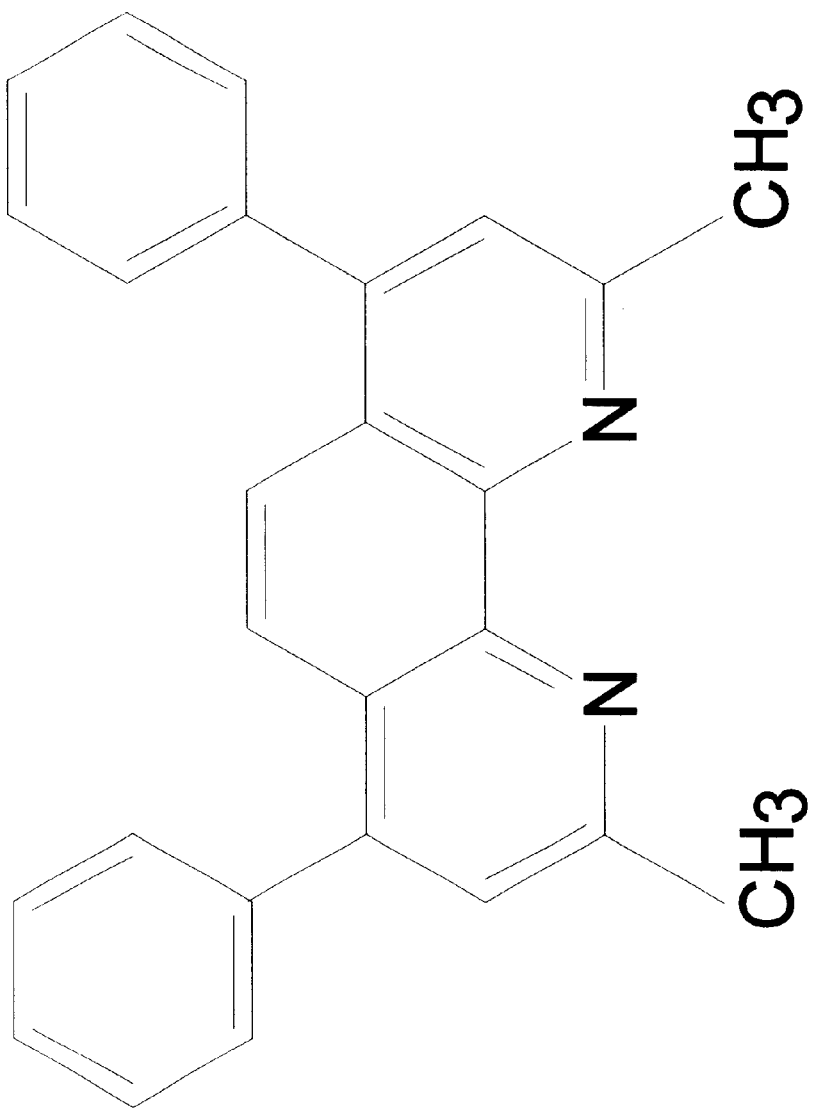
FIG. 4 shows the chemical formula for BCP.

The present invention will now be described in detail for specific preferred embodiments of the invention. These embodiments are intended only as illustrative examples and the invention is not to be limited thereto.

The present invention is directed to a novel cathode comprised of a metal-doped organic electron injection layer that is in direct contact with a transparent, non-metallic, electron injecting cathode layer, such as ITO, wherein the metal-doped organic electron injection layer also functions as an exciton blocking layer and/or as a hole blocking layer. The metal-doped organic electron injection layer is created by diffusing an ultra-thin layer of a highly electropositive metal throughout the layer. Such cathodes may be employed in a wide range of organic optoelectronic devices, such as OLEDs, solar cells, photodetectors, lasers and phototransistors. OLEDs incorporating such cathodes are shown herein to have what are believed to be the highest reported combination of transparency and total device external quantum efficiency for an OLED.

A particular feature of the present invention is the use of an ultra-thin layer of an electropositive metal, such as lithium, which is allowed to diffuse throughout the organic election injection layer that is typically immediately adjacent an electron injecting cathode material such as ITO. An ultra-thin layer refers to a layer that is only of the order of about 5–10 Å thick. Since the electropositive metal can readily diffuse throughout the electron injection layer, the electropositive metal may be deposited on either side or both sides of the electron injection layer.

For example, after preparing a typical sequence of OLED layers, that is, a substrate, an anode, a hold transporting layer (HTL), an optional separate emissive layer, and an electron transporting layer (ETL), the electropositive metal may be deposited as an ultra-thin metal layer directly on the electron transporting layer. The electron injection layer is then deposited on the ultra-thin metal layer. The electron injecting ITO layer would then be deposited on the organic electron injection layer.

Alternatively, he organic electron injection layer may be deposited on the electron transporting layer (ETL), with the electropositive metal layer being thereafter deposited on the organic electron injection layer. In this case, the electron injecting ITO layer is then deposited on the electropositive metal layer.

In each case, it is believed, based on the evidence provided herein, that the electropositive metal diffuses throughout the electron injection layer so as to produce a highly or degenerately doped electron injection layer, in which free electrons are donated to the electron injection layer by the electropositive metal. An electropositive metal refers to a metal that readily loses or gives up electrons, for example, the elements in Groups 1, 2 and 3, or elements in the lanthanide group, of the periodic table. Preferred electropositive metals include, for example, Li, Sr and Sm, with Li being the most preferred electropositive metal.

Since the ultra-thin metal layers are limited to thickness of only about 5–10 Å, it is believed that the electropositive metal diffuses substantially in its entirety into the electron injection layer, such that, after such diffusion, the ultra-thin metallic layer is no longer on the surface of the electron injecting layer. Thus, the entire cathode, which includes both the electron injection ITO layer and the electron injection layer, may be referred to as being non-metallic since the cathode does not contain a separate metallic layer. The metal elements that are present, indium and tin in the ITO layer, are each present in their chemically combined oxide form, whereas the electropositive metals such as lithium are diffused throughout the electron injection layer and, thus, are not present in a metallic form.

The present invention is distinguished from the compound cathodes of U.S. Pat. No. 5,703,436, which include a Mg/Ag layer that typically is of the order of at least about 75–100 Å thick, though layers as thin as 50 Å were disclosed therein. Such compound cathodes, thus, include a separate, but relatively thin, metallic layer. While such compound cathodes were shown to have a sufficiently high transparency such that functional transparent OLEDs could be fabricated, the overall OLED transparency was nevertheless limited by the absorption and reflection losses of the thin metallic layer of the compound cathode. The cathodes of the present invention do not include such a metallic layer. The cathodes of the present invention, thus, do not suffer from the disadvantage of having metallic layers that can cause transparency losses due to absorption and reflection, such as are exhibited by metal layers having a thickness of 50 Å or greater.

It is believed that diffusion of the electropositive metal into the electron injection layer can create a highly degenerately doped layer that enhances election injection into the OLED. More specifically, it is believed that the electropositive material donates electrons to the organic electron injection layer, thereby increasing the conductivity of the electron injection layer to the point that band bonding occurs to aid in the injection of charge into the layer. An increased conductivity results in a reduced barrier for injecting electrons into the electron injection layer, as compared with conventional devices that do not contain an electropositive metal doped in the electron injection layer. A reduction in the electron injection barrier results in a reduced operating voltage for devices that contain the metal doped electron injection layer.

In the representative embodiments of the present invention in which lithium is doped in a BCP layer, it is believed that diffusion of the electropositive lithium metal into the BCP layer creates a highly degenerate metal-doped BCP layer. However, highly doped metal layers that are not doped sufficiently to become fully degenerate are also believed to be capable of functioning within the scope and spirit of the present invention. While it may not be known exactly what fraction of the metal atoms that diffuse into the electron injection layer may contribute to the measurable or charge-carrying electronic density of the layer, the metal atom density in the layer may be selected so as so be sufficient to produce a theoretically expected electronic density, based on the assumption that each metal atom contributes just one charge carrying electron to the molecules in the electron injection layer. For example, based on this assumption, the metal atom density in the layer may be selected so as to produce an electronic density between $10^{15}/cm^3$ and $10^{22}/cm^3$. A metal-doped layer according to the present invention, thus, has a metal atom density of at least about $10^{15}/cm^3$, and preferably a metal atom density of at least about $10^{21}/cm^3$.

Alternatively, the metal atom density in the electron injection layer can be tailored for producing a total external quantum efficiency greater than the efficiency of an OLED that uses a thick metallic cathode, while also achieving a much greater transparency. More specifically, the metal atom density in the electron injection layer may be selected to be sufficient to produce a total external quantum efficiency of the OLED of at least one percent.

A further feature of the present invention is the use of an exciton blocking and/or a hole blocking material as the organic electron injection layer that is doped with the electropositive metal. By choosing a material that permits the metal-doped organic electron injection layer to function as an exciton blocking layer, the metal-doped organic electron injection layer serves to block diffusion of excitons into the layer, thus allowing more of the excitons within the emission layer to contribute to device efficiency. A material that is used as the exciton blocking layer in an OLED may be defined as a material that has an exciton energy, defined as the energy difference between the electron and hole in a ground state exciton, that is greater than the energy of the excitons that are produced in the emission layer of the OLED. Because of the coulomb forces between the nearby electron and hole in a around state exciton, the exciton energy of an organic material is typically slightly less than the energy difference between the lowest unoccupied molecular orbital (LUMO) and the highest occupied molecular orbital (HOMO) of the material.

By choosing a material that permits the metal-doped organic electron injection layer to function as a hole blocking layer, the metal-doped organic electron injection layer serves to block diffusion of holes into the layer, thus allowing more excitons to be created within the emission layer so as to contribute to a higher device efficiency. The metal-doped organic electron injection, layer, thus, may function as an exciton blocking layer, as a hole blocking layer, or as both an exciton blocking layer and a hole blocking layer.

Since the electron injection layer also has the function of conducting charge carriers, in particular, electrons, the ionization potential (IP) and band gap of the electron injection material are such as to provide efficient charge carrier flow into the adjacent electron transporting layer. The requirements and characteristics of these materials are, thus, as described in the applications having U.S. application Ser. Nos. 09/153,144, filed Sep. 14, 1998, now U.S. Pat. No. 6,097,147, and 09/311,126, filed May 13, 1999, now abandoned, which are incorporated in their entirety by reference.

Furthermore, in each case, an additional layer or layers may be present between one or more of the sequential pairs of these layers. For example, for a double heterostructure, a separate emissive layer is included between the hole transporting layer and the electron transporting layer. This separate emissive layer may be characterized as being a thin luminescent layer. Alternatively, or in addition, a hole injection enhancement layer may be present between the anode layer and the hole transporting layer. In addition, the emissive layer may be comprises of either fluorescent or phosphorescent emission materials.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a metal-doped organic electron injection layer that is in direct contact with a transparent, non-metallic, electron injecting cathode layer, such as ITO, wherein the metal-doped organic electron injection layer also functions as an exciton blocking layer and/or as a hole blocking layer.

The cathodes of the present invention may be incorporated into an optoelectronic device that is included in a vehicle, a computer, a television, a printer, a large area wall, theater or stadium screen, a billboard, a laser or a sign, although not limited to only these devices. The devices disclosed in the following patents or co-pending patent applications, each of which is incorporated herein in its entirety, may benefit from incorporation of the non-metallic cathodes of the present invention: U.S. Pat. Nos. 5,703,436; 5,707,745; 5,721,160; 5,757,026; 5,757,139; 5,811,833; 5,834,893; 5,844,363; 5,861,219; 5,874,803; 5,917,280; 5,922,396; 5,932,895; 5,953,587; 5,981,306; 5,986,268; 5,986,401; 5,998,803; 6,005,252; 6,013,538; and 6,013,982; and U.S. patent application Ser. No. 08/779,141, now U.S. Pat. No. 5,986,268; Ser. No. 08/821,380, now U.S. Pat. No. 5,986,401; Ser. No. 08/977,205, now U.S. Pat. No. 6,013, 538; Ser. No. 08/865,491, now U.S. Pat. No. 5,998,803; and Der. No. 08/928,800, now U.S. Pat. No. 5,981,306. The materials, methods and apparatus disclosed in these patents and co-pending applications may also be used to prepare the OLEDs of the present invention.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

EXAMPLES OF THE INVENTION

A representative embodiment of the present invention was prepared using a compound cathode comprising 2,9-dimethyl-4,7 diphenyl-1,10-phenanthroline (BCP) as the electron injection layer and inserting an ultra-thin film of about 5–10 Å of lithium (Li), an electropositive metal, into this layer, which was in contact with an electron injecting ITO layer. This compound cathode structure was used in an OLED having a total external quantum efficiency of $(1.0\pm0.05)\%$ at a drive current of 10 mA/cm$^2$, with a transparency of about 90%, or higher, across the entire visible spectrum. This is believed to be the highest reported combination of transparency and total device external quantum efficiency for an OLED. OLEDs having a total external quantum efficiency of at least 1.0% and a transparency of at least 90% are, thus, herein referred to as highly efficient and highly transparent OLEDs.

These results suggest that Li readily diffuses throughout the BCP layer, degenerately doping the BCP. The degenerately doped electron injection layer of BCP acts as an exciton blocking layer, and the Li acts as an electron donor, creating a doped degenerate surface layer to enhance electron injection into the OLED. In one preferred embodiment the degenerate doping of the BCP is controlled leading to an electronic density of at least $10^{21}$/cm$^3$. At these densities, the layer of BCP is a degenerate semiconductor which establishes an ohmic contact with the bulk organic semiconductor. See the inset of FIG. 8.

Four sets of transparent, non-metallic OLEDs were fabricated on precleaned and ultraviolet-ozone treated ITO coated glass substrates to positively demonstrate the transparency and efficiency benefits of a compound cathode employing an exciton blocking layer. All transparent devices were fabricated without a vacuum break. For purposes of comparison, 650 Å of the hole-transporting layer (HTL) 4,4-bis[N-(1-naphthyl)-N-phenyl-amino] biphenyl ((α-NPD) was vacuum (base pressure of $10^{-7}$ Torr) deposited on the ITO, followed by 750 Å of the emissive, electron-transporting layer (ETL): tris-(8-hydroxyquinoline) aluminum (Alq$_3$). A 1500 Å thick Mg:Ag (10:1 mass ratio) cathode followed by a 500 Å cap of Ag was then deposited onto the Alq$_3$ surface through a shadow mask to form the conventional, control OLEDs. Then, three devices including an exciton blocking layer employing the following cathode variations, deposited in reverse sequence: a) ITO/BCP; b) ITO/BCP/Li; and c) ITO/Li/BCP. The thickness of the ITO was about 525 Å, but could have ranged from 100 to 2000 Å. The BCP was about 70 Å, but could have functioned as an effective injection and exciton blocking layer in a range from 20 to 500 Å. The Li layer was about 5–10 Å, but the layer thickness may be varied with the thickness of the BCP layer, such that the lithium produces an electronic density of at least about $10^{15}/cm^3$, and more preferably at least about $10^{22}/cm^3$, remaining functional between about $10^{15}/cm^3$ and $10^{22}/cm^3$, but not necessarily limited to $10^{22}/cm^3$, depending on the materials chosen. The ITO was radio-frequency magnetron sputtered from a 10 cm diameter target at a power of 50 W, an Ar flow rate of 140 sccm, and a pressure of 2 mTorr, yielding a deposition rate of 0.3 Å/s. N. Johansson, T. Osada, S. Stafstrom, W. R. Salaneck, V. Parente, D. A. dos Santos, X. Crispin, and J. L Bredas, *J. Chem. Phys.* 111, 2157 (1999). Elemental Li in the form of a rod was thermally evaporated at a rate of 1 Å/s. However, the cathode could work equally well using other methods of ITO, BCP and lithium deposition. Alternatively, the lithium and BCP may be co-deposited.

Figure 5:
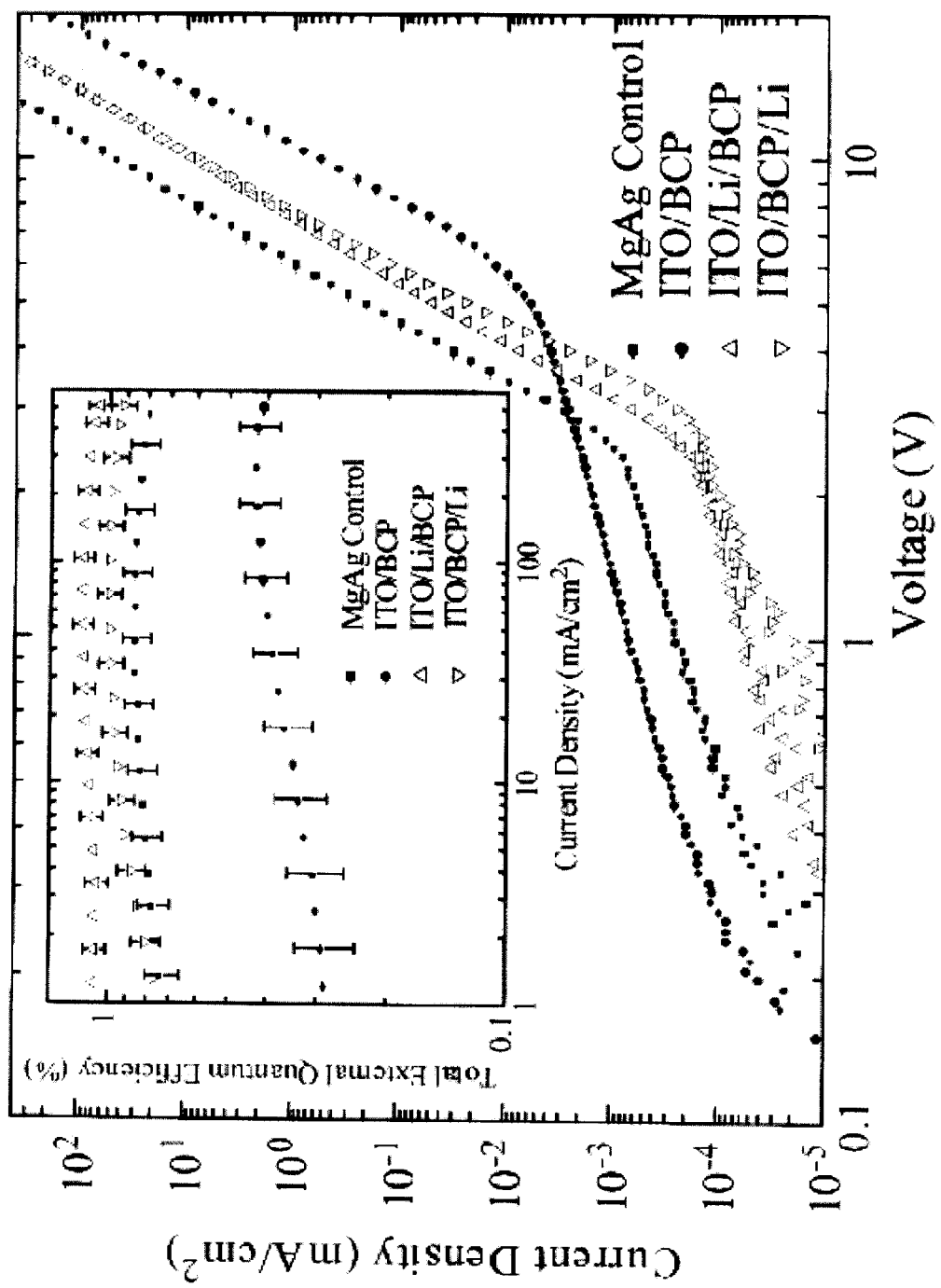
FIG. 5 shows the current-density vs. voltage (J-V) plot of OLEDs with the following structure: cathode/$Alq_3$/α-NPD/ITO where the cathode is Mg:Aa, ITO/BCP, TTO/Li/BCP, and ITO/BCP/Li and the Inset shows the total external quantum efficiency (η) vs. current density (J) for these four.

The four devices had similar current density-voltage (J-V) characteristics. The graph in FIG. 5 shows two distinct, characteristic regimes for charge transport in small molecule OLEDs: ohmic transport at low drive voltages following J~V, and trapped-charge limited transport at higher drive voltages following J~$V^m$, where m is typically in the range 5–10 at room temperature. G. Parthasarathy, P. E. Burrows, P. Tian, I. G. Hill, A. Kahnr and S. R. Forrest, J. Appl. Phys., 86, 4067 (1999); P. E. Burrows, Z. Shen, V. Bulovic, D. M. McCarty, S. R. Forrest, J. A. Cronin, and M. E. Thompson, *J. Appl. Phys.* 79, 7991 (1996). The "operation voltage" is obtained at a current density of 10 mA/cm$^2$, corresponding to a luminance of about 100 cd/m$^2$, the nominal requirement for video applications. Both the Li-containing and Mg:Ag contact devices have similar operating voltages of about 9 V (to within about 1 V). However, the conventional non-metallic device without Li shows a marked increase to 14.5 V. This is believed to be caused by the large injection barrier at the ITO/BCP interface. In all cases, the low voltage regime shows a very low leakage current density of less than or equal to about $10^{-5}$ A/cm$^2$, although the Li-free devices had a somewhat higher leakage. Yield, defined as the ratio of non-shorted to the total number of devices tested, for each of the four sets of devices was 100% for a sample size of 16.

The total external quantum efficiencies of the devices are plotted in the inset of FIG. 5. For the transparent devices, the optical output power is the sum of that emitted from both the substrate and the cathode surfaces. At J=10 mA/cm$^2$, the OLED with the metallic cathode had $\eta$=(0.85±0.05)% while the transparent devices containing Li had $\eta$=(1.0±0.05)%. However, the transparent device without Li shows $\eta$=(0.30±0.05)%, consistent with previous unpublished results. Again, this provides evidence of a significant barrier to the transfer of electrons from the conducting layer to the blocking layer or the blocking layer to the device or both, leading to imbalanced injection of charge and thus a lower $\eta$.

The insertion of 5–10 Å of Li is known to improve the external quantum efficiency of non-metallic OLEDs. L. S. Hung and C. W. Tang, *Appl. Phys. Lett.* 74, 3209 (1999). Previous results show that a layer of Li that is too thick causes a reduction in $\eta$, ultimately eliminating the benefit achieved by introducing Li into the BCP layer. Therefore, the preferred thickness of the lithium layer falls in an optimum range, which depends on the electronic density of the exciton blocking layer.

In addition, by using BCP, as an exciton blocking layer, and also as a hole blocking layer, instead of CuPc, an increase in the external quantum efficiency of about 40% is shown. This improved efficiency is significant, providing marked improvement in brightness or power consumption.

To make these cathodes useful for integration in full color displays, it is desirable to have high transparency across the entire visible spectrum, thus further motivating the use of a degenerately-doped, exciton blocking, and/or as a hole blocking, cathode instead of CuPc/Li, the latter cathodes being only 65% to 85% transparent in the visible, whereas the cathode with the layer of BCP is about 90% or higher across the entire visible spectrum.

Figure 6:
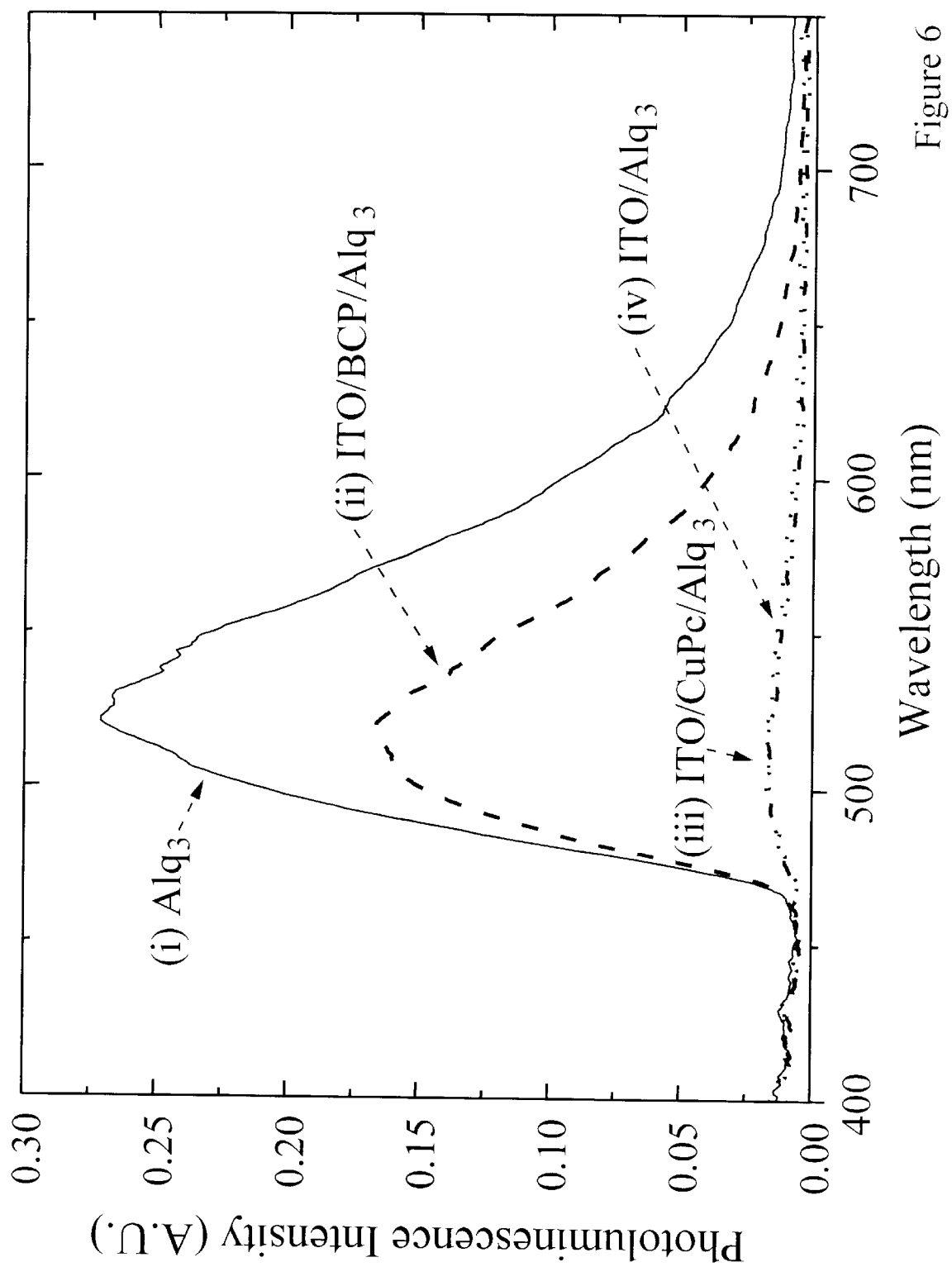
FIG. 6 shows photoluminescence intensity (arbitrary units) vs. wavelength of the following structures grown on quartz: (i) $Alq_3$; (ii) ITO/BCP/$Alq_3$; (iii) ITO/CuPc/$Alq_3$; and (iv) ITO/$Alq_3$.

To understand the losses incurred when using CuPc instead of BCP beneath the ITO contact, the relative photoluminescence (PL) efficiencies were measured for the following structures, which were grown on Quartz: (i) Alq$_3$; (ii) ITO/BCP/Alq$_3$; (iii) ITO/CuPc/Alq$_3$; and (iv) ITO/Alq$_3$. The thickness of the Alq$_3$ was 100 Å, the CuPc and BCP was 70 Å, and the ITC cap was 525 Å. A mercury lamp in conjunction with a 10 nm wide optical band pass filter centered at the wavelength of $\lambda$=400 nm was used as the excitation source incident via the quartz substrate, creating excitons uniformly throughout the Alq$_3$ layer P. E. Burrows, Z. Shen, V. Eulovic, D. M. McCarty, S. R. Forrest, J. A. Cronin and M. E. Thompson, *J. Appl. Phys.* 79, 7991 (1996). Further, CuPc is nearly transparent at $\lambda$=400 nm, eliminating effects due to exciton generation in that layer. Parthasarathy, P. E. Burrows, V. Khalin. V. G. Kozlov, and S. R. Forrest, *Appl. Phys. Lett.* 72, 2138 (1998). FIG. 6 shows that the ratio of the PL efficiencies for structures (i):(ii):(iii):(iv) are 16:10:1:1. Since the thicknesses of the organic layers and the ITO were kept constant, and ITO is transparent at the wavelengths studied, microcavity effects do not play a significant role in determining the shape or intensity of the PL spectra in the figure. It may be concluded, therefore that BCP prevents the dramatic quenching of Alq$_3$ excitons due to the sputter induced damage from the ITO at the cathode. S. Parthasarathy, G. Gu and S. R. Forrest, *Adv. Mat.* 11, 907 (1999). BCP acts effectively in blocking exciton transport to the damaged ITO/organic interface. In contrast, CuPc does not appear to significantly reduce quenching compared to that observed by direct deposition of ITO onto Alq$_3$.

Figure 7:
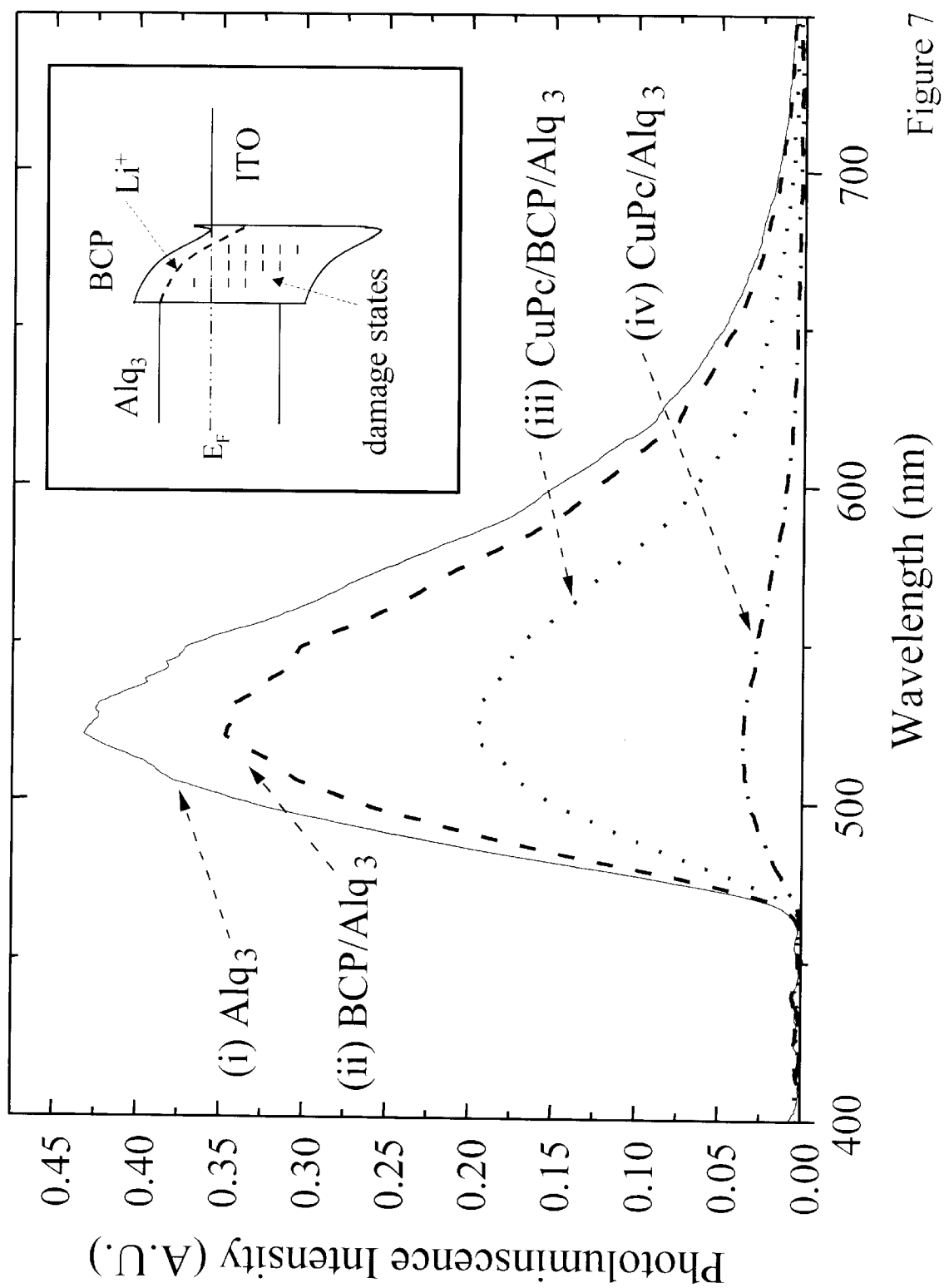
FIG. 7 shows photoluminescence intensity vs. wavelength of the following structures grown on quartz: (i) $Alq_3$; (ii) BCP/$Alq_3$; (iii) CuPc/BCP/$Alq_3$; and (iv) CuPc/$Alq_3$, with an Inset figure that shows the proposed energy level diagram of the degenerately doped BCP/$Li^+$ layer having a constant Fermi level ($E_F$) at thermal equilibrium and damage states which are due to ITO deposition, and assist in efficient electron injection.

To separate the quenching of Alq$_3$ emission due to the presence of CuPc from that due to the sputter damage under the ITO, the following second set of structures was grown on quartz with the same thicknesses as above: (i) Alq$_3$; (ii) BCP/Alq$_3$; (iii) CuPc/BCP/Alq$_3$; and (iv) CuPc/Alq$_3$. The ratio of the PL efficiencies for structures (i):(ii):(iii):(iv) are 12:10:6:1, as shown In FIG. 7. This shows that CuPc itself quenches Alq$_3$ emission, possibly via exciplex formation at the organic heterostructure interface. In addition, these experiments indicate that BCP, previously shown to be a barrier to Alq$_3$ exciton transport, can be placed between CuPc and Alq$_3$ to partially recover the Alq$_3$ PL intensity by preventing excitons from migrating to the damaged region immediately below the sputtered ITO contact.

It Is known that Li diffuses through organics. E. I. Haskel, A. Curioni, P. F. Seidler and W. Andreoni, Appl. Phys. Lett.

68, 2606 (1997); N. Johansscn, T. Osada, S. Stafstrom, W. R. Salaneck, V. Parente, D. A. dos Santos, X. Crispin and J. L. Bredas, *J. Chem. Phys.* 111, 2157 (1999). Thus, it is not surprising that placing Li on either side of the BCP layer makes no significant difference in the device characteristics. However, it was reported that the Insertion of Li between CuPc and Alq$_3$ resulted in a substantial increase in the operating voltage when compared to inserting Li between CuPc and the ITO cap. L. S. Hung and C. W. Tang, *Appl. Phys. Lett.* 74, 3209 (1999). This discrepancy was not observed with the CuPc/Li system. The difference between the present results and the previous results may be attributed to the method of fabrication of the top ITO contact. The present data, combined with the fact that Li acts to improve electron injection, suggests that Li dopes the BCP layer by donating its valence electron, thereby forming Li$^-$ ions. This doping results in band bending, reducing the barrier to charge injection from the ITO contact into the bulk of the Alq$_3$. Assuming a bulk density of 0.53 g/cm$^3$, 10 Å of Li can donate up to $10^{16}$ electrons/cm$^2$ into a layer of BCP of thickness of about 100 Å, leading to an electronic density of about $10^{21}$ electrons/cm$^3$. By depositing a thicker continuous layer of Li, the Li atoms are tied to the surface, consequently reducing both diffusion and doping. This explains why Li thicknesses much greater than 10 Å were ineffective in producing high efficiency OLEDs when deposited upon a layer of BCP of about 100 Å.

Figure 8:
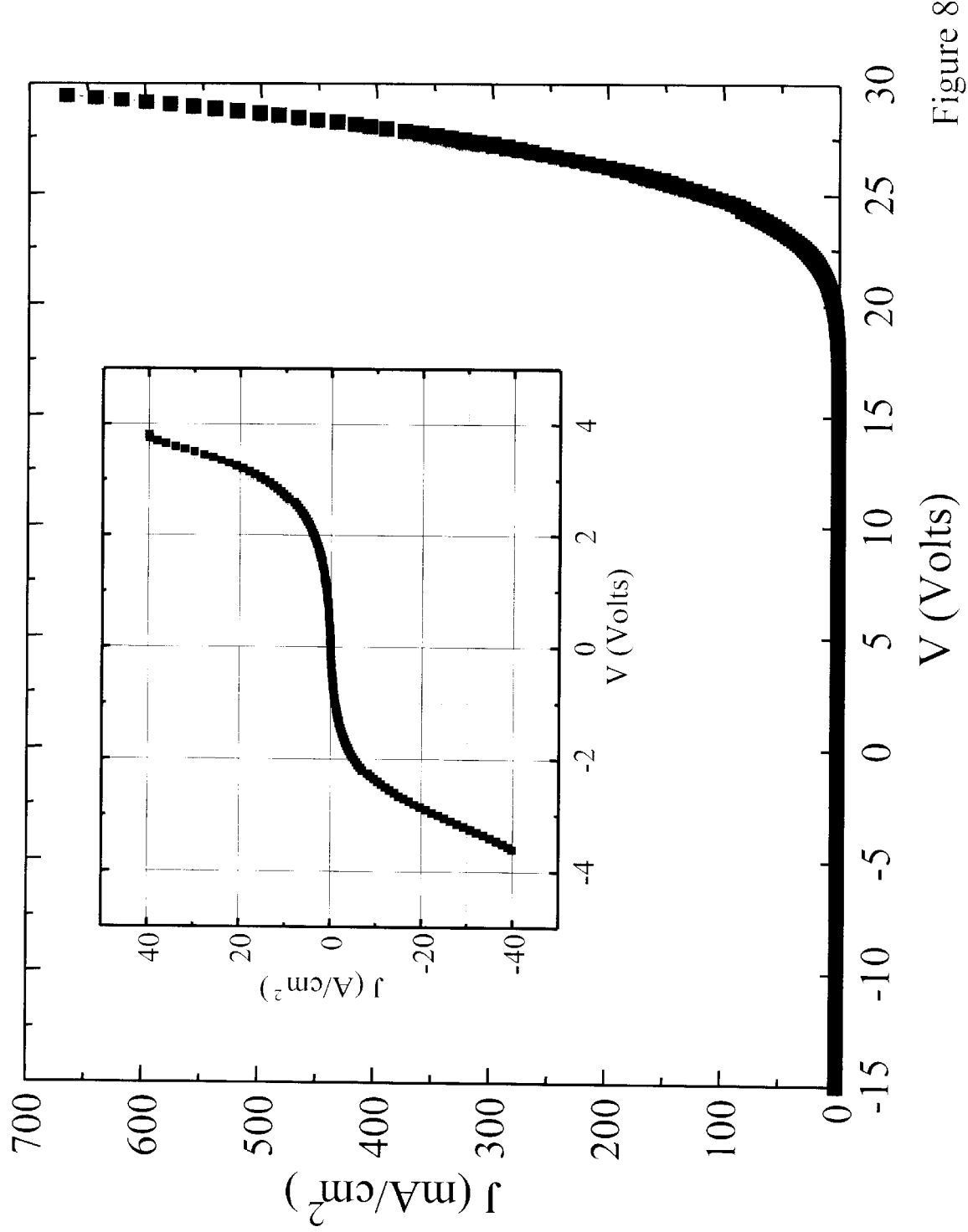
FIG. 8 shows current-density vs. voltage (J-V) characteristics of a Ag/BCP/ITO device. Inset: J-V characteristics of the same device in FIG. 4 with the addition of ~10 Å of Li at the Ag/BCP interface.

To test the hypothesis of Li$^+$ diffusion and doping, simpler structures of the form: 1500 Å Ag/800 Å BCP/ITO were fabricated with and without about 10 Å Li at the Ag/BCP interface. As shown in FIG. 8, the Li-free device has a rectification ratio of about $10^5$ measured at ±30 V. In contrast, the device containing about 10 Å of Li between the BCP and the Ag shows nearly ohmic behavior at low V, with a contact resistance of about 1 Ω-cm$^2$. This allows for very large currents densities (about 40 A/cm$^2$) at very low voltages (about 2 V) with a rectification ratio of about 1 at ±3.5 V. It may be inferred from these data that Li diffuses throughout the 800 Å BCP layer, degenerately doping the BCP to yield a highly conductive layer air enabling efficient electron injection. N. Johansson, T. Osada, S. Stafstroin, W. R. Salaneck, V. Parente, D. A. dos Santos, X. Crispin and J. L. Bredas, *J. Chem. Phys.* 111, 2157 (1999). Therefore, BCP degenerately doped with Li is a preferred exciton blocking layer.

What is claimed is:

1. A highly transparent and highly efficient organic light emitting device comprising, in the following order:

an anode layer comprising ITO;

a hole transporting layer comprising 4,4-bis[N-(1-naphthyl)-N-phenyl-amino]biphenyl;

an electron transporting layer comprising tris-(8-hydroxyquinoline) aluminum; and a cathode, further comprising a lithium-doped electron injection layer comprising 2,9-dimethyl-4,7-diphenyl-1,10-phenanthroline, and an ITO layer in contact with said lithium-doped electron injection layer.

2. A compound cathode comprising a transparent, non-metallic, electron injecting material in contact with an organic electron injection layer doped with a metal, wherein the organic electron injection layer comprises a transparent organic material that acts as a hole blocking layer, wherein the transparent organic material is 2,9-dimethyl-4,7-diphenyl-1,10-phenanthroline.

3. The compound cathode of claim 2, wherein said metal is selected from the group consisting of Li, Sr and Sm.

4. The compound cathode of claim 2, wherein said metal is Li.

5. The compound cathode of claim 2, wherein said metal produces an electronic density of at least about $10^{15}$/cm$^3$.

6. The compound cathode of claim 2, wherein said metal produces an electronic density of at least about $10^{21}$/cm$^3$.

7. The compound cathode of claim 2, wherein said transparent, non-metallic, electron injecting material comprises indium tin oxide.

8. The compound cathode of claim 2, wherein said compound cathode is incorporated in an organic optoelectronic device.

9. The compound cathode of claim 8, wherein said optoelectronic device is an organic light emitting device.

10. The compound cathode of claim 9, wherein said organic light emitting device is incorporated in a device selected from the group consisting of a vehicle, a computer, a television, a printer, a screen, a billboard, a display and a telephone.

11. The compound cathode of claim 2, wherein said organic electron injection layer has a thickness of about 20 angstroms to about 500 angstroms.

12. The compound cathode of claim 2, wherein said organic electron injection layer has a thickness of about 70 angstroms.

13. The compound cathode of claim 2, wherein said metal diffuses throughout said organic electron injection layer.

14. A compound cathode comprising a transparent, non-metallic, electron injecting material in contact with an organic electron injection layer comprising 2,9-dimethyl-4,7-diphenyl-1,10-phenanthroline doped with Li.

15. The compound cathode of claim 14, wherein said transparent, non-metallic, electron injecting material comprises indium tin oxide.

* * * * *